United States Patent
Ott et al.

(10) Patent No.: US 10,329,251 B2
(45) Date of Patent: Jun. 25, 2019

(54) INITIATOR FOR PREPARING ALKANESULFONIC ACIDS FROM ALKANE AND OLEUM

(71) Applicant: Grillo-Werke AG, Duisburg (DE)

(72) Inventors: Timo Ott, Duisburg (DE); Ingo Biertümpel, Duisburg (DE)

(73) Assignee: Grillo-Werke AG, Duisburg (DE)

( * ) Notice: Subject to any disclaimer, the term of this patent is extended or adjusted under 35 U.S.C. 154(b) by 0 days.

(21) Appl. No.: 15/035,865

(22) PCT Filed: Nov. 17, 2014

(86) PCT No.: PCT/EP2014/074747
§ 371 (c)(1),
(2) Date: May 11, 2016

(87) PCT Pub. No.: WO2015/071455
PCT Pub. Date: May 21, 2015

(65) Prior Publication Data
US 2016/0289181 A1    Oct. 6, 2016

(30) Foreign Application Priority Data

Nov. 18, 2013  (EP) .................... 13193349

(51) Int. Cl.
| C07C 303/06 | (2006.01) |
| C07C 409/44 | (2006.01) |
| C07C 309/00 | (2006.01) |
| C07C 407/00 | (2006.01) |

(52) U.S. Cl.
CPC .......... *C07C 409/44* (2013.01); *C07C 303/06* (2013.01); *C07C 309/00* (2013.01); *C07C 407/00* (2013.01)

(58) Field of Classification Search
None
See application file for complete search history.

(56) References Cited

U.S. PATENT DOCUMENTS

| 2,493,038 A | 1/1950 | Synder et al. |
| 2,619,507 A | 11/1952 | Jones et al. |
| 4,680,095 A | 7/1987 | Wheaton |
| 4,910,335 A | 3/1990 | Wheaton |
| 5,154,912 A | 10/1992 | Schirmann et al. |
| 5,304,360 A * | 4/1994 | Lane .................... B01J 19/2415 422/161 |
| 7,119,226 B2 | 10/2006 | Sen et al. |
| 7,282,603 B2 | 10/2007 | Richards |
| 2005/0070614 A1 | 3/2005 | Richards |
| 2007/0282151 A1* | 12/2007 | Richards ................ C07C 1/322 585/733 |
| 2008/0161591 A1 | 7/2008 | Richards |
| 2016/0289176 A1 | 10/2016 | Ott et al. |

FOREIGN PATENT DOCUMENTS

| CN | 1732141 A | 2/2006 |
| EP | 1558353 B1 | 6/2016 |
| WO | 2004041399 A2 | 5/2004 |
| WO | 2005069751 A2 | 8/2005 |
| WO | 2007136425 A2 | 11/2007 |
| WO | 2015071351 A1 | 5/2015 |
| WO | 2015071365 A1 | 5/2015 |
| WO | 2015071371 A1 | 5/2015 |
| WO | 2015071455 A1 | 5/2015 |

OTHER PUBLICATIONS

Haskins Biomedical Mass Spectrometry 1982, 9(7), 269-277.*
Willstätter et al.; "On the Knowledge of Caro's Acid", Chemical Laboratory of the Schweizerisches Polytechnikum of Zurich, 27 pages (Apr. 26, 1909).
Second Office Action of CN Patent Application No. 201480061403.5; dated Oct. 26, 2017; 16 pages.
Korth et al.; "Direct Spectroscopic Detection of Sulfonyloxyl Radicals and First Measurements of Their Absolute Reactivities1A", Journal Physics Chemical, 94, 8835-8839 (1990).

* cited by examiner

*Primary Examiner* — Ana Z Muresan
(74) *Attorney, Agent, or Firm* — Christensen, Fonder, Dardi & Herbert PLLC; Curtis Herbert

(57) ABSTRACT

A compound of the formula:
$$CH_3—SO_2—O—O—SO_2OH.$$

4 Claims, 1 Drawing Sheet

INITIATOR FOR PREPARING ALKANESULFONIC ACIDS FROM ALKANE AND OLEUM

CROSS REFERENCE TO RELATED APPLICATIONS

This application is a national stage filing of PCT Application Number PCT/EP2014/074747 filed Nov. 17, 2014, which claims priority to European Patent Application Number 13193349.1 filed Nov. 18, 2013, both of which are hereby incorporated herein by reference.

TECHNICAL FIELD

The present invention relates to a compound that can be employed as an initiator for manufacturing of alkanesulfonic acids, especially methanesulfonic acid, from alkane, especially methane, and oleum, to processes for manufacturing the compound according to the invention, and to a process for manufacturing of alkanesulfonic acid, especially methanesulfonic acid, using the compound according to the invention as an initiator, and to the use of the compound according to the invention in a device for performing the process for manufacturing of alkanesulfonic acid, especially methanesulfonic acid.

BACKGROUND

Alkanesulfonic acids are organic acids that can reach a similar acid strength as that of inorganic mineral acids, for example, sulfuric acid. However, in contrast to usual mineral acids such as sulfuric and nitric acids, the sulfonic acids are non-oxidizing and do not give off vapors that are harmful to health, as can be observed with hydrochloric and nitric acids. Further, many sulfonic acids, for example, methanesulfonic acid, are biologically degradable. The applications of sulfonic acids are many, for example, in cleaning agents, surfactants, as catalysts, and in organic synthesis, pharmaceutical chemistry, for example, as protective groups. The salts of sulfonic acids are employed, for example, as surfactants, for example, sodium dodecylsulfonate, or in the electroplating industry, especially as tin, zinc, silver, lead and indium, but also other metal, alkylsulfonates. The very high solubility of alkyl sulfonates plays an important role, in particular. Further, no harmful gases are formed in electrolysis, and the use of toxic compounds, for example, cyanide, which is common in many cases, is dispensed with.

The structurally simplest representative of alkanesulfonic acids is methanesulfonic acid. U.S. Pat. No. 2,493,038 describes the preparation of methanesulfonic acid from $SO_3$ and methane. US 2005/0070614 describes further methods for preparing methanesulfonic acid, and its application. The methods known in the prior art are in part complicated, cost-intensive, and lead to undesirable products because of the harsh conditions.

The reaction conditions in conventional processes of alkanesulfonic acid production can result in undesirable side products, which even manifest themselves as disturbing inhibitors in the production of alkanesulfonic acids. This may lead to termination of the actual reaction for preparing the alkanesulfonic acid, but also to impurities, formation of side products and poor yields, based on sulfur trioxide and methane.

INTRODUCTION AND SUMMARY OF THE INVENTION

WO 2007/136425 A2 discloses the use of the compound di(methanesulfonyl) peroxide (DMSP), which must be prepared by a complex electrolysis and, in addition, is a crystallizable highly explosive solid, as an initiator in a reaction in which methanesulfonic acid is formed from sulfur trioxide and methane.

It is the object of the present invention to provide a compound that can be employed for the manufacturing of alkanesulfonic acids from alkane, especially methane, and sulfuric trioxide or oleum, allowing for an improved reaction control.

The object of the invention is achieved by a compound of the formula I

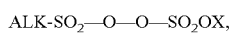

wherein ALK is an alkyl group, especially a methyl, ethyl, propyl, butyl, isopropyl, isobutyl group, or a higher alkyl group, and X=hydrogen, zinc, aluminium, an alkali or alkaline earth metal.

In particular, the compound according to the invention is present in a mixture of the invention which contains additionally at least one compound selected from the group consisting of formula II to XI, i.e. II, III, IV, V, VI, VII, VIII, IX, X, or XI:

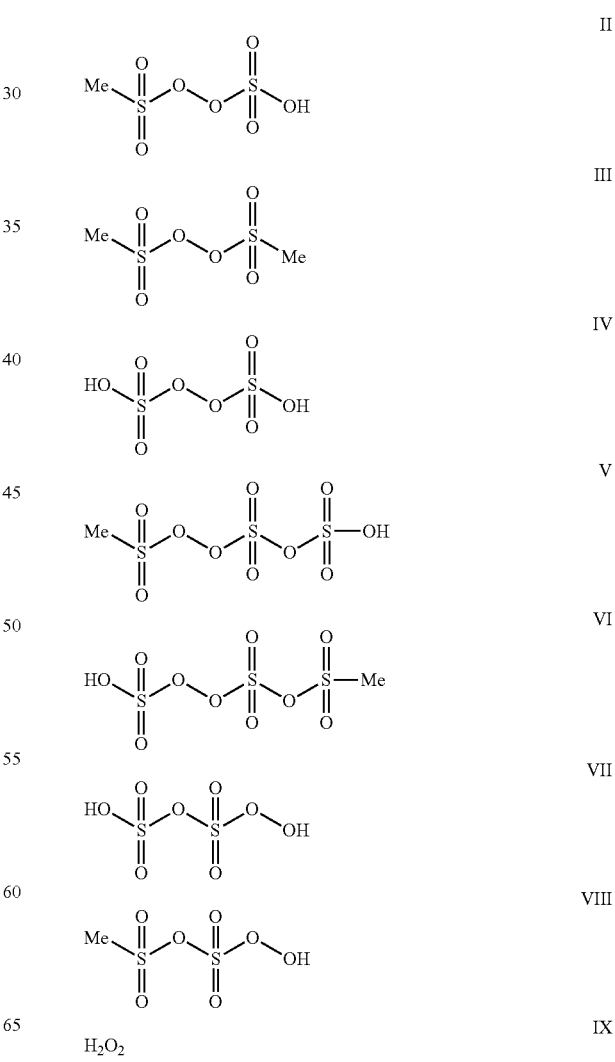

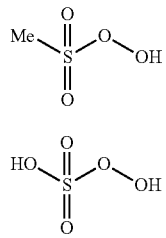

and combinations thereof.

In another embodiment the compound of the invention or the mixture of the invention is present in sulfuric acid or alkanesulfonic acid, especially methanesulfonic acid.

For example, the compound according to the invention with X=H can be manufactured by a process comprising the following steps:
reacting alkanesulfonic acids, especially methanesulfonic acid, with hydrogen peroxide;
then adding oleum;
followed by the isolation of the compound.

In particular, the isolation can be effected by extraction, chromatography, precipitation, recrystallization, freeze-drying or similar methods under mild conditions.

In a particular embodiment of the process according to the invention, the isolation can be effected by means of precipitation or chromatography. Inert support materials and inert solvents, such as sulfuric or sulfonic acids, are employed therein. The use of organic solvents is also possible.

Inert support materials are in particular those which do not negatively interfere with components being the actual reaction partners, e.g. by reducing the yield of the compound of the invention. Furthermore, inert support materials can either chemisorb or physisorb—or both—a chemical compound, without destroying its functionality or structure in an irreversible way. Examples are materials based on e.g. silicon dioxide, aluminium oxide, zirconium oxide and the like.

A mono-alkali peroxosulfate or alkaline earth peroxosulfate is reacted with alkanesulfonic acid halide, especially methanesulfonic acid halide, and the compound according to the invention can be separated from the alkali or alkaline earth halide formed. The alkali or alkaline earth halides formed can be removed by extraction or precipitation to obtain the pure peroxosulfate.

Another way to prepare the peroxosulfate product (X=H) is to react a mono-alkylperoxosulfate with chloro-, or bromo-sulfonic acid. The alkali or alkaline earth halides formed can be removed by extraction or precipitation to obtain the pure peroxosulfate.

If X=aluminium, zinc, alkali or alkaline earth metal, the respective compound can be obtained by an addition of the respective aluminium, zinc, alkali or alkaline earth metal alkaline base.

The invention also relates to the use of the compound according to the invention or of the mixture according to the invention as an initiator in a chemical reaction for manufacturing alkanesulfonic acids, especially methanesulfonic acid, from methane and oleum.

The invention also relates to a process for manufacturing of alkanesulfonic acids, especially methanesulfonic acid, comprising the steps stated below:

A solution containing sulfur trioxide or oleum is reacted with an alkane in a reactor. For alkanes with a low boiling point, the use of a high-pressure reactor is necessary. For pentane and higher alkanes, a common laboratory reactor is sufficient. In the case of gaseous alkanes, for example, methane, a pressure of 1-150 bar gas pressure is set. The initiator is added to this solution. The initiator is prepared by reacting an alkanesulfonic acid or a solution of such alkanesulfonic acid in a solvent with hydrogen peroxide, and optionally isolated. The concentration of the hydrogen peroxide may be 20-100% (w/w). Subsequently, the reaction is completed at 0-100° C. The raw product can be processed by extraction, crystallization, distillation or chromatography.

The invention further relates to the use of the compound of the invention in a device for performing the process according to the invention, wherein the device is comprising a first reactor 1 in which sulfur trioxide and alkane, especially methane, react with the compound according to the invention as initiator, a second reactor 2 in which the compound according to the invention is formed, a distillation means 3 for distilling the product formed in the first reactor 1, and a filling means 4, connections from reactor 2 to reactor 1, from reactor 1 to the distillation means 3, and from the distillation means 3 to each of the filling means 4, the second reactor 2, and the first reactor 1.

DETAILED DESCRIPTION

Figure 1:
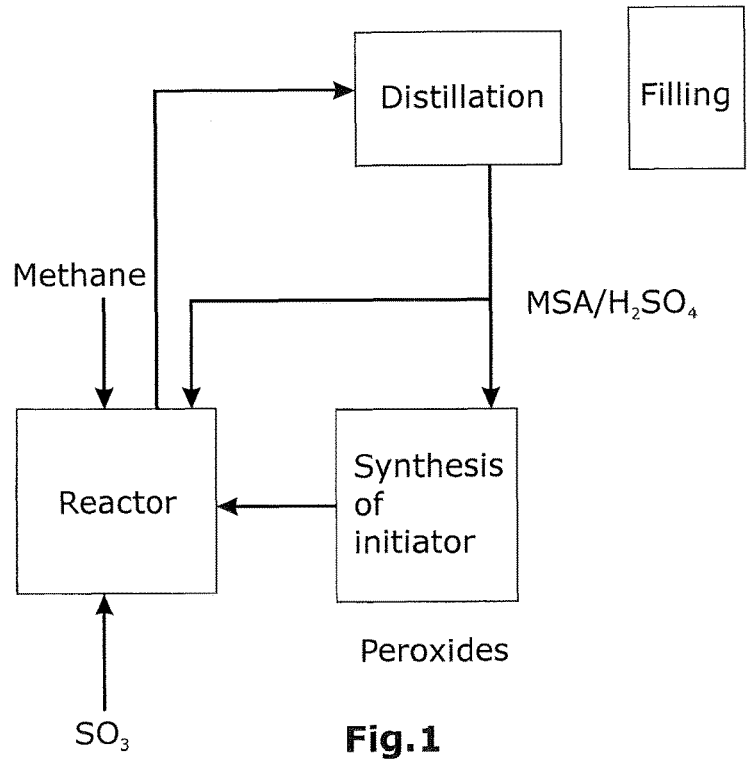
FIG. 1 shows schematically, in an exemplary way, a simple system according to the invention for the manufacturing of methanesulfonic acid according to the invention.
Figure 2:
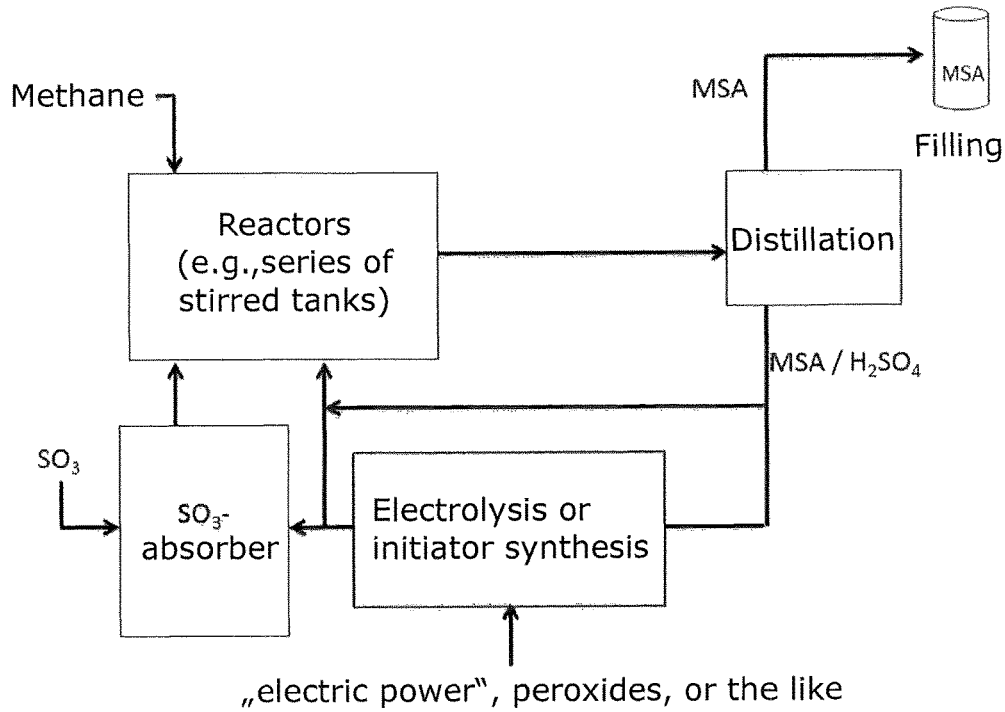
FIG. 2 shows a schematic layout of a preferred device.

The process according to the invention allows for alkane sulfonation, especially methane sulfonation, in a reactor system using oleum with alkane, especially methane, with addition of the compound according to the invention as an initiator. Advantageously, the raw product can be purified by distillation, which already yields a relatively pure alkanesulfonic acid, especially methanesulfonic acid, as a distillate.

The residue consists of sulfuric acid with a content of up to 10% alkanesulfonic acid, especially methanesulfonic acid (MSA). These distillation bottoms may be used 1) as a solvent for the continuous reaction in the reactor; 2) for the preparation of "fresh" oleum with pure sulfur trioxide; 3) by reacting hydrogen peroxide (30% to 100% (w/w) solution in water), the compound according to the invention can be prepared, which may be employed as an initiator or precursor for it.

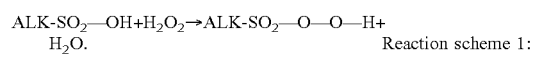

Reaction scheme 1:

The compound according to the invention is capable of reacting with oleum to form a mixed acid peroxide. This yields the initiator, the compound according to the invention.

Reaction scheme 2:

This mixed peroxo anhydride is characterized by a high reactivity as compared to DMSP (dimethylsulfonyl peroxide, $H_3CSO_2$—O—O—$SO_2CH_3$), which is known from the prior art, for example, and which causes longer reaction times. At the same time, however, the selectivity of the DMSP in view of the formation of side products is obtained. In contrast, peroxodisulfuric acid (Marshall's acid) is very reactive and very little selective. The compound according to the invention combines the selectivity of DMSP with the reactivity of Marshall's acid.

In the following, the invention is further illustrated in an exemplary way taking the preparation of methanesulfonic acid as an example.

Example 1

Preparation of the Initiator Solution

To a mixture consisting of 90 ml of 100% sulfuric acid and 10 ml of methanesulfonic acid, 3.4 ml of 70% (w/w) hydrogen peroxide is added dropwise with external cooling and intensive stirring.

Synthesis Protocol:

In a 3.75 L autoclave, 1000 g of 36% (w/w) oleum is charged, and the temperature controlled to 50° C. After a pressure of 100 bar of methane gas was set, intensive stirring is performed with a stirrer from the company Parr. Now, the initiator solution is metered dropwise to the solution. The pressure drops to 35 bar within 5 hours. The yield is higher than 90%, based on sulfur trioxide. The reaction product contains 42% (w/w) methanesulfonic acid.

Example 2

Preparation of the Initiator Solution

To a mixture consisting of 90 ml of 100% sulfuric acid and 10 ml of methanesulfonic acid, 3.4 ml of 70% (w/w) hydrogen peroxide is added dropwise with external cooling and intensive stirring.

Synthesis Protocol:

In a 3.75 L autoclave, 1000 g of 36% (w/w) oleum is charged, and the temperature controlled to 35° C. After a pressure of 100 bar of methane gas was set, intensive stirring is performed with a stirrer from the company Parr. Now, the initiator solution is metered dropwise to the solution. The pressure drops to 35 bar within 5 days. The yield is higher than 90%, based on sulfur trioxide. The reaction product contains 42% methanesulfonic acid.

Characterization of Monomethylsulfonyl Peroxide:

Using different analytical techniques monomethylsulfonyl peroxide was characterized. Using mass spectroscopy the molecular weight was determined as M=191.94 g/mol. The $^1$H-NMR ($D_2SO_4$) shows a signal for the Methylgroup at 3.43 ppm. A suitable way in order to measure the peroxide content is titration (Jander, Jahr, Maßanalyse, Theorie und Praxis der Titrationen mit chemischen und physikalischen Indikationen, 17. Auflage, Walter de Gruyter GmbH 2009, Berlin).

The invention claimed is:

1. A compound of the formula $CH_3$—$SO_2$—O—O—$SO_2OH$.

2. A mixture comprising the compound of claim 1 and sulfuric acid, alkylsulfonic acid, methanesulfonic acid, or combinations thereof.

3. A process for manufacturing the compound according to claim 1 comprising:

reacting an alkanesulfonic acid with a hydrogen peroxide; then adding oleum;

followed by the isolation of the compound.

4. The process according to claim 3, wherein said separating is effected by precipitation or chromatography.

* * * * *